United States Patent [19]

Yang

[11] Patent Number: 4,476,732
[45] Date of Patent: Oct. 16, 1984

[54] SEPTUMLESS JET STREAM ON-COLUMN INJECTOR FOR CHROMATOGRAPHY

[75] Inventor: Frank J. Yang, Danville, Calif.

[73] Assignee: Varian Associates, Inc., Palo Alto, Calif.

[21] Appl. No.: 487,372

[22] Filed: Apr. 21, 1983

[51] Int. Cl.³ .............................................. G01N 1/10
[52] U.S. Cl. ............................... 73/863.73; 73/864.81
[58] Field of Search ........... 73/864.81, 864.82, 864.83, 73/864.84, 863.72, 863.73

[56] References Cited

U.S. PATENT DOCUMENTS

| | | | |
|---|---|---|---|
| 3,122,168 | 2/1964 | Wright | 73/864.81 X |
| 3,730,002 | 5/1973 | Penton | 73/864.82 |
| 3,940,994 | 3/1976 | Klee et al. | 73/864.81 |
| 3,991,055 | 11/1976 | Godin et al. | 73/864.84 X |
| 4,300,393 | 11/1981 | Stearns | 73/864.81 X |
| 4,346,610 | 8/1982 | Ishii et al. | 73/863.73 |

*Primary Examiner*—Gerald Goldberg
*Assistant Examiner*—Joseph W. Roskos

*Attorney, Agent, or Firm*—Stanley Z. Cole; Norman E. Reitz; Keiichi Nishimura

[57] ABSTRACT

A plunger seats in the outlet end of a cavity formed in an injector housing. The plunger is moveable within the cavity between seated engagement with the outlet end and a position which permits fluid to flow out the outlet end. The cavity is sealed to withstand pressures on the order of 2000 bar. A groove formed in the wall of the plunger or in the wall of the cavity receives liquid sample from a sample feed line which is formed in the body of the housing and terminates adjacent the groove when the plunger is seated in the outlet end of the cavity. A source of mobile phase fluid is connected to the upper end of the cavity by an inlet line. By external displacement means, the plunger is moved out of seated engagement within said cavity to permit a jet stream of mobile phase fluid to sweep the sample from the sample groove out through the outlet end of the cavity and onto a chromatographic column connected to the injector housing.

13 Claims, 8 Drawing Figures

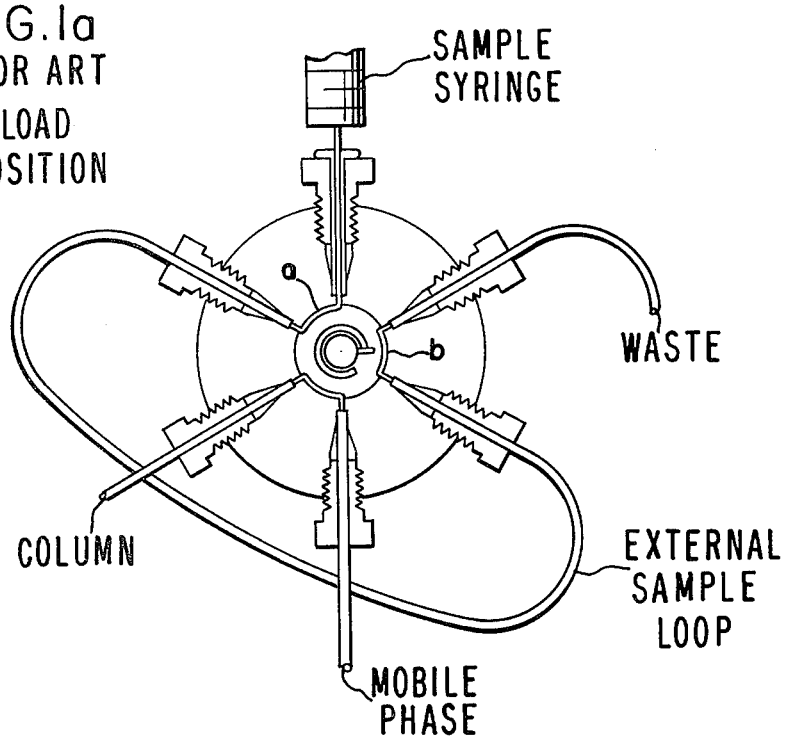
FIG.1a PRIOR ART LOAD POSITION
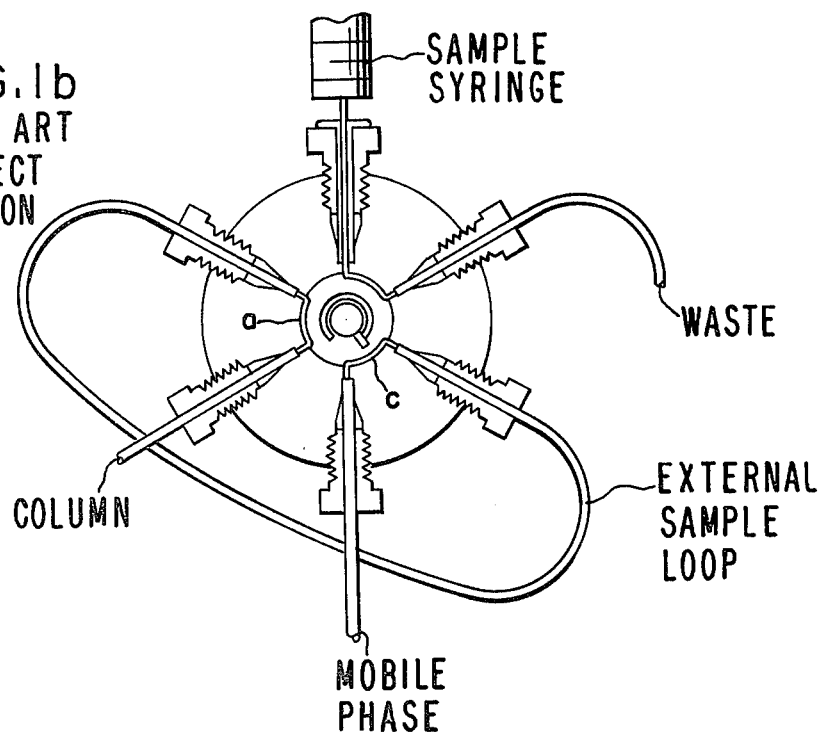
FIG.1b PRIOR ART INJECT POSITION

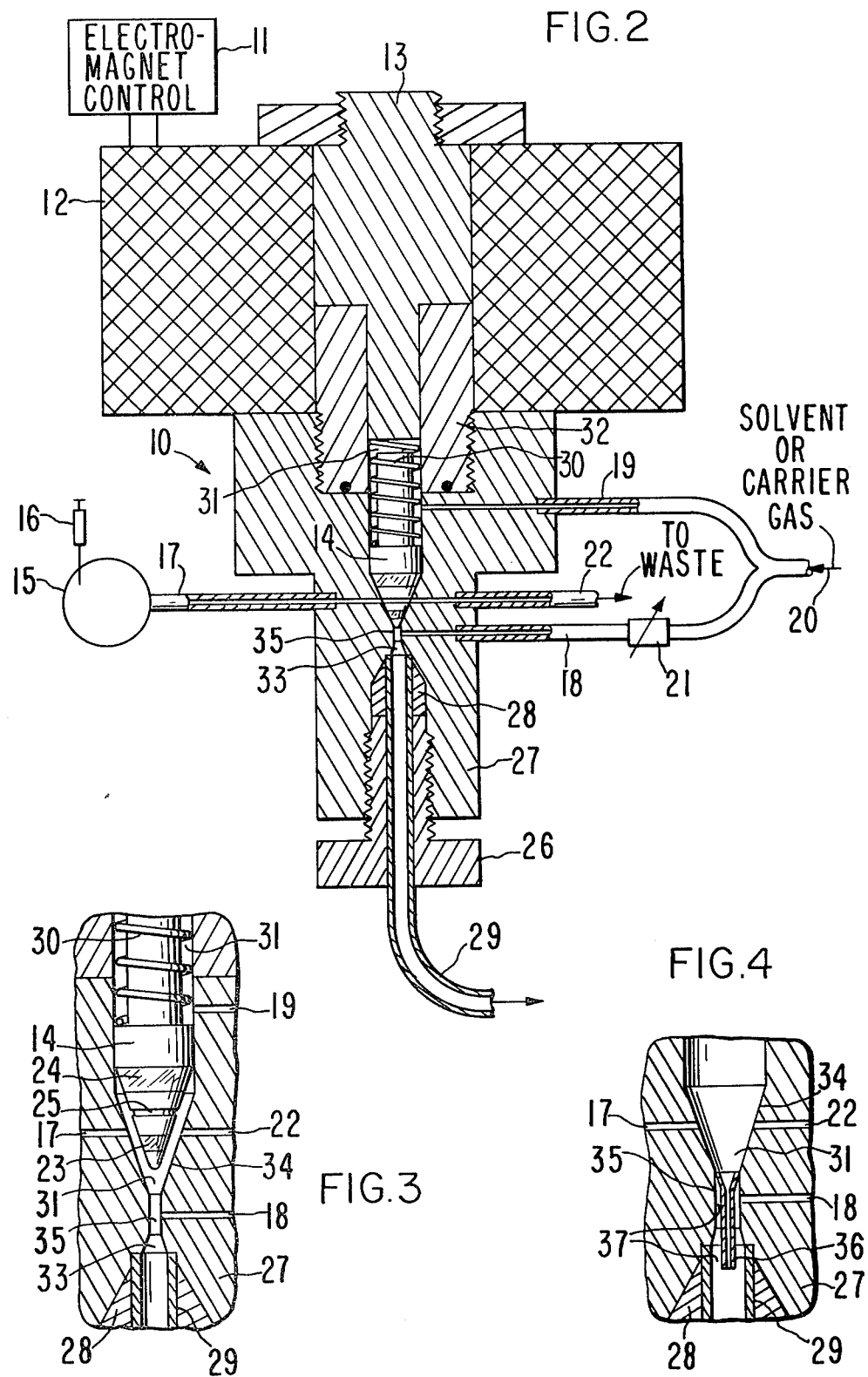

SEPTUMLESS JET STREAM ON-COLUMN INJECTOR FOR CHROMATOGRAPHY

This invention relates to an injector for introducing a sample into a chromatograph and, more particularly, relates to a jet stream on-column injector for introducing small liquid samples into a chromatograph.

The injection of small liquid samples into chromatographs in a controlled manner is becoming increasingly important. In liquid chromatography prior art sampling systems include micro-valve loop injectors and syringe type injectors which introduce the sample via a syringe. With such injectors the minimum injectable sample sizes are limited to the fixed volumes of the loop or syringe. Severe dead volume effects may also be present. And sampling at pressures higher than 5000–7000 psi is not yet possible; yet even within this pressure range the valves deteriorate rapidly due to surface-to-surface abrasion. In gas chromatography with split, splitless or direct injection the portion of the sample entering the column may not always be completely representative of the original sample due to effects such as thermal decomposition, mass discrimination and selective evaporation. See, e.g., G. Schomburg, et al., "Sampling Techniques in Capillary Gas Chromatography", J. Chrom., v. 142, pp. 87–102 (1977).

So-called on-column injectors have been used in gas chromatography. With on-column injectors a syringe needle is inserted directly into the open end of the column and the sample is injected onto the column without exposure to an intermediate heated region. This is desirable to avoid thermal decomposition and the separation of volatile components. See, e.g., G. Sisti, et. al., "Method and Device for Sample Injection Under Controlled Conditions of Temperature Profile Into Gas Chromatograhic Columns", U.S. Pat. No. 4,269,608; K. Grob, et al., "On-Column Injection Onto Gas Capillary Columns, J. of Chromatography, v. 151, p. 311 (1978); and K. Grob, "On-Column Injection Onto Capillary Columns", part 2, J. High Res Chrom & Chrom Comm., p. 263 Nov. 1978). These injectors have not been suitable for high pressure injection because injection does not occur within a sealed region. Also, the size of the syringe needle limits the smallest compatible column inner diameter to about 0.2 mm.

It is therefore an object of the present invention to provide an on-column injector suitable for gas and liquid chromatography which will permit injection of small liquid samples at pressures up to several thousand bar.

It is another object of the present invention to provide a septumless on-column injector which will permit injection of small volumes of liquid in a controllable manner.

It is a further object of the present invention to provide an on-column injector which utilizes a jet stream to rapidly sweep a small liquid sample directly onto a chromatographic column.

It is an additional object of the present invention to provide an on-column injector for chromatography which allows curtain flow injection directly onto a chromatographic column.

BRIEF DESCRIPTION OF THE DRAWINGS

For a more complete understanding of the apparatus of the present invention reference may be had to the accompanying drawings which are incorporated herein by reference and in which:

FIGS. 1a and 1b are planar cross-sectional views of a micro-valve closed loop injector of the prior art;

FIG. 2 is a side view of the jet stream injector of the present invention connected to a chromatographic column;

FIG. 3 is an expanded view of the seal between the plunger and restricted passageway leading to the connection with the chromatographic column;

FIG. 4 is an expanded view of the injector housing as modified for curtain flow injection;

SUMMARY OF THE INVENTION

Figure 5:
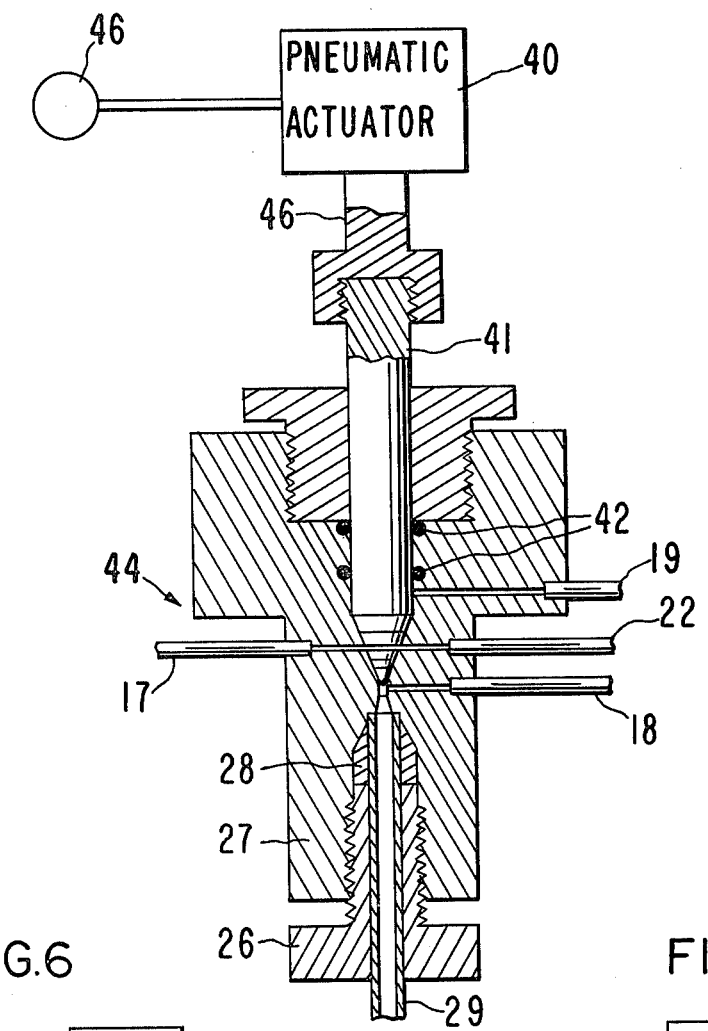
FIG. 5 is a side view of the jet stream injector of the present invention incorporating pneumatic amplifier control.

A plunger seats in a precisely mated cavity formed in an injector housing. The plunger is moveable within the cavity to be out of seated engagement with said cavity. The cavity is sealed to withstand pressures by the order of 2000 bar. A groove formed in the wall of the plunger or the housing receives a liquid sample from a sample feed line which is formed in the body of the housing and terminates adjacent the groove when the plunger is seated in said cavity. A source of mobile phase fluid is connected to the upper end of the cavity. By external means, the plunger is raised to permit a jet stream of mobile phase fluid from the source of mobile phase to sweep the sample through a restricted passageway opening at the bottom of the cavity and onto a chromatographic column connected to the injector housing.

DESCRIPTION OF THE PREFERRED EMBODIMENT

The need for reliable injectors in chromatography is heightened as sample sizes are reduced and operating pressures are increased. This is particularly true for liquid chromatography and holds to a lesser extent for gas chromatography. Inherently, the injection of a sample onto a chromatographic column is not readily susceptible to high pressure operation since any system which allows penetration of the interior volume during injection must necessarily seal off the avenue by which injection was accomplished during the operation of the chromatograph. For example, a soft septum may permit penetration but does not function as a high pressure seal. Even the best loop injectors which rely on precisely machined, mated surface-to-surface seals are limited to pressures of the order of 300–500 atmospheres or less. These injectors must often be repaired due to the occurrence of internal leakage. These types of injectors hold a sample in either an external or internal sample loop. The loop is filled and discharged through narrow grooves etched in the circumference of a rotor. During loading, as shown in FIG. 1a, groove a connects a sample syringe with the external sample loop. Sample is forced from the syringe, through the external sample loop and out groove b to waste. Once the external sample loop is full, the rotor is rotated to an inject position, shown in FIG. 1b, where groove a now connects one end of the external sample groove with the column. Groove c connects the other end of the external sample loop with the source of the mobile phase. The sample in the groove is then flowed onto a chromatographic column by the mobile phase. Sample sizes are limited to the capacity of the sample loop and appreciable time may be taken in rotating the mated members from one station to another under high pressure. See also D. Ishii, et al., "Device For Introducing Micro Amount of Sample Into an Analyzing Apparatus", U.S. Pat. No. 4,346,610.

The septumless jet stream on-column injector of the present invention achieves the desirable features for a controllable low sample volume injector for chromatography. It experiences little band spreading, is scalable, and may be used with conventional autosamplers such as the Varian Model 8000. It accomplishes these ends because there is no external sample loop and because the sample is placed in a small groove which is instantaneously exposed to a jet stream of a mobile phase rather than being serially fed onto a column as is carried out in the prior art shown in FIGS. 1a and 1b. Preferably, the groove is placed in the center of the jet stream. And, preferably, the jet stream is subsequently injected onto the column in a curtain flow mode, as described in detail below. In any of these embodiments, there is no significant dispersion of the sample either spatially or temporally as it is swept onto the column. For gas chromatography the injector can be heated for sample vaporization or the liquid sample is vaporized upon entering the heated column inlet or vaporization zone.

The jet stream on-column injector 10 of the present invention is shown in cross-sectional view in FIG. 2. An injector body 27 is threadably attached to sleeve 32 which fits over electromagnet core member 13. Injector body 27 contains an upper cavity 31 which houses a plunger 14. Plunger 14 is spring-loaded to seat in the bottom of cavity 31 in this embodiment by spring 30 which presses against the bottom protrusion of electromagnet core member 13. In other embodiments the differential pressure of inlet line 19 over inlet line 18 will produce seating of plunger member 14. When electromagnet core 12 is not energized, plunger 14 is seated against the mated bottom 34 of cavity 31 by the action of spring 30; see especially FIG. 2. The bottom of cavity 31 is shaped as an inverted cone to precisely receive the plunger 14 in mated liquid-tight relationship. When electromagnet 12 is energized by means of electromagnet control 11, the plunger is raised above the inverted conical surface 34 as seen particularly in FIG. 3.

A chromatographic column 29 seats in the upper end of cavity 33 formed in the lower portion of injector body 27. The end of column 29 is surrounded by ferrule 28 which is held in place by threaded end nut 26. While plunger 14 remains seated, there is a steady flow of carrier gas or solvent 20 onto column 29 through inlet line 18.

Sample is introduced to the groove 25 when the plunger is in its seated position. Alternately, the groove may be formed in the wall of inverted conical surface 34. The isolation of groove 25 from the upstream mobile phase line 19 (carrying carrier gas or liquid solvent) is aided by an elastomeric coating 24 of material such as Teflon ® or Kel-F ® which forms a fluid-tight seal with inverted conically shaped surface 34. The isolation of groove 25 from mobile phase inlet line 18 and from cavity 33 is aided by a similar elastomeric coating 23 which also forms a fluid-tight seal with inverted conically shaped surface 34. During sample loading, a sample is flowed through sample line 17, around groove 25 and out waste line 22. Sample may be provided to sample line 17, for example, by syringe 16 and loop injector 15 such as a Rheodyne Model 7060 injector. Once sample groove 25 is full of sample and the injection loop is closed, injection may be carried out. During injection no excess sample is drawn into the jet stream from sample line 17 or waste line 22 because of a positive pressure gradient compressing samples in the sample line 17 and waste line 22 away from the mobile solvent flow stream in the cavity 31.

As shown in FIG. 3, plunger 14 will be raised upwardly when electromagnet 12 is energized. Incoming solvent or carrier gas from inlet line 19 will stream around the base and conical portion of plunger 14 and sweep sample from groove 25 out the bottom of cavity 31 through restricted passageway 35 and into column 29. The direction of jet stream flow around plunger 14 will always be downward and out of cavity 31 since the pressure of solvent or carrier gas from inlet line 19 will always exceed that of inlet line 18. This results from the presence of flow restrictor 21 in inlet line 18 (shown in FIG. 2) and the fact that lines 18 and 19 have a common source line 20.

Figure 6:
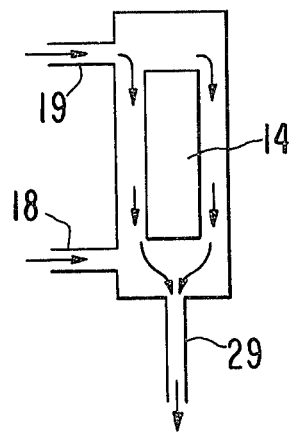
FIG. 6 is a schematic illustration of the flow during conventional injection.

A schematic diagram showing the direction of of flow of mobile phase fluid is shown in FIG. 6. Fluid enters both lines 18 and 19, but flows downwardly around plunger 14, into restricted passageway 35 and onto column 29.

An alternate embodiment of the injector of FIG. 2 is shown in partial view in FIG. 4. The alternate embodiment is identical to that shown in FIG. 2 except for the region around restricted passageway 35; this region where differences exist is specifically depicted in FIG. 4. A tubular insert 36 extends between the bottom of cavity 31 and the open end of column 29. The sample and mobile phase are thus injected directly into the central region of the column. An annular region 37 is defined between tubular insert 36 and the walls of restricted passageway 35. Within this region the flow of mobile phase from inlet line 18 flows in around tubular insert 36 and down past its tip. Thus, at the point of injection onto the column the sample and mobile phase mixture are surrounded by a curtain of mobile phase. The sample thus does not reach the walls until it is fully injected onto the column and therefore cannot adhere to the column walls. The sample is uniformly distributed onto the column.

Figure 7:
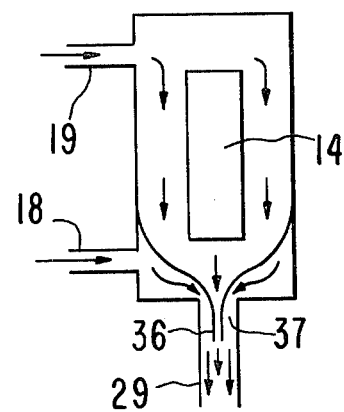
FIG. 7 is a schematic illustration of the flow during curtain flow injection.

The flow of solvent or carrier gas in the alternate embodiment of FIG. 4 thus enshrouds the sample. Classical curtain flow is disclosed, for example, in the following references. See T. J. N. Webber, et al., "Optimization of Liquid Chromatographic Performance on Columns Packed with Microparticulate Silicas", J. Chromatogaphy, v. 122, pp. 243-258 (1976); J. J. Kirkland, et al., "Sampling and ExtraColumn Effects in High-Performance Liquid Chromatography . . . ", J. Chromatographic Science, v. 15, pp. 303-316 (1977). The flow during curtain flow injection is shown schematically in FIG. 7. Mobile phase flows in lines 18 and 19. Due to the higher pressure in line 19, the flow proceeds downwardly around plunger 14 and into tubular insert 36. The flow is channeled downwardly and exits the tip of tubular insert 36 and onto column 29. The short arrows depict the flow of sample and mobile phase. Simultaneously, mobile phase from line 18 flows down around tubular insert 36 through annular region 37 and thence into column 29. The flow of mobile phase is depicted by the long arrows. The long arrows form a curtain around the short arrows. The sample does not reach the walls; it is uniformly distributed onto the column.

In the embodiment shown in FIGS. 2-3, the sample groove describes a circumference of plunger 14. In other embodiments the groove may be axial or arbitrarily shaped, providing the groove may readily be filled from a sample inlet line. Or, as described above, the groove may be in the wall of the cavity. In still other embodiments the plunger may have a shape other than conical so long as it is precisely mated with a shaped seat.

Another embodiment of the on-column injector of the present invention is shown in FIG. 5. The bottom portion of injector 44 from the sample groove down is fabricated in accordance with FIGS. 2, 3 or 4. The upper portion employs a linear displacement means shown to be pneumatic amplifier 40 to control the position of plunger 41. The piston 45 of pneumatic actuator 40 is affixed to the upper end of extended plunger 41. This pneumatic actuator is, for example, of the type of Rheodyne Model 5001. The connection and operation of pneumatic actuator 40 and plunger 41 is akin to the showing of FIG. 3 at p. 5106 of F. Yang, et al., "Determination of Precise and Reliable Gas Diffusion Coefficients by Gas Chromatography", J. of American Chemical Society, v. 98, Aug. 18, 1976. Upon actuation by introducing a gas from gas source 46, the piston 45 is drawn upward thereby unseating the plunger 41 in injector 44. A high pressure seal capable of withstanding pressures up to 2,000 bar (approx. 30,000 psi) is produced by staged O-rings 42 which contact the cylindrical body of plunger 41. In a preferred embodiment a smooth sapphire shaft is used for plunger 41 to facilitate the obtaining of a good seal. In yet other embodiments an arrangement analogous to the embodiment of FIG. 5 can be used with other positive actuators, typically not requiring spring loading, being employed in lieu of pneumatic actuator 40. These include electrical (solenoid) actuators, mechanical linkage and hand operated plungers (typically requiring spring biasing to seat the plunger in the injector.

What is claimed is:

1. A jet stream on-column injector for injection of a liquid sample directly onto a chromatographic column, comprising:
    an injector body having an interior cavity sealed from ambient, and having a sample feed line for introducing sample to a sample groove formed on a surface within said cavity, and having a mobile phase feed line for introducing a mobile phase under pressure to the inlet end of said cavity;
    a plunger member positioned within said cavity, said plunger member sealingly engaging with the outlet end of said cavity; and
    displacement means attached to said plunger, said displacement means being capable of producing linear displacement of said plunger to thereby withdraw said plunger from said sealed engagement with said outlet end of said cavity whereby a jet stream of said mobile phase flows around the exterior of said plunger and sweeps said sample from said groove through the exit end of said injector body.

2. A jet stream on-column injector in accordance with claim 1 wherein said injector body has means adjacent its outlet end for accepting said chromatographic column in fluid tight relationship whereby said sample is flowed onto said chromatographic column and whereby said injector body has means for introducing a constant flow of mobile phase onto said column downstream of said outlet end of said cavity.

3. An on-column injector in accordance with claim 2 wherein said sample groove is formed in the wall of said cavity, said sample groove being in fluid flow comunication with said sample feed line.

4. An on-column injector in accordance with claim 2 wherein said sample groove is formed in the surface of the tip of said plunger, said sample groove being in fluid flow communication with said sample feed line when said plunger is in said sealed engagement with the outlet end of said cavity.

5. A jet stream on-column injector in accordance with claim 2 in combination with sample injection means in fluid communication with said sample feed line.

6. A jet stream on-column injector in accordance with claim 2 wherein said displacement means comprises a pneumatic actuator.

7. A jet stream on-column injector in accordance with claim 2 in combination with bias means for forcing said plunger into sealed engagement with the outlet end of said cavity.

8. A jet stream on-column injector in accordance with claim 6 wherein said displacement means comprises mechanical linkage.

9. A jet stream on-column injector in accordance with claim 6 wherein said displacement means comprises a magnet and wherein said plunger means is fabricated from ferromagnetic material.

10. A jet stream on-column injector in accordance with claim 8 wherein said magnet is an electromagnet positioned above said ferromagnetic plunger member.

11. A jet stream on-column injector in accordance with claim 2 wherein said plunger member has a cylindrical shank with a conical tip, the tip of said plunger fitting in mated, sealed engagement with the outlet end of said cavity.

12. A jet stream on-column injector in accordance with claim 10 wherein said small sample groove comprises a circumferential indentation around the middle of said conical tip of said plunger.

13. A jet stream on-column injector in accordance with claim 11 wherein the surface of said plunger above and below said sample groove is coated with a compressible elastomeric material to facilitate a seal between said sample groove and, respectively, the upper portion of said cavity and the outlet end of said injector body.

* * * * *